United States Patent
Dorian et al.

(10) Patent No.: US 11,672,892 B2
(45) Date of Patent: Jun. 13, 2023

(54) APPARATUS AND METHODS FOR CONCENTRATING PLATELET-RICH PLASMA

(71) Applicant: Hanuman Pelican, Inc., New Orleans, LA (US)

(72) Inventors: Randy Dorian, San Diego, CA (US); Michael D. Leach, Warsaw, IN (US); Richard W. Storrs, Berkeley, CA (US); Scott R. King, New Orleans, LA (US)

(73) Assignee: Hanuman Pelican, Inc., New Orleans, LA (US)

( * ) Notice: Subject to any disclaimer, the term of this patent is extended or adjusted under 35 U.S.C. 154(b) by 0 days.

(21) Appl. No.: 18/146,835

(22) Filed: Dec. 27, 2022

(65) Prior Publication Data
US 2023/0134453 A1 May 4, 2023

Related U.S. Application Data

(63) Continuation of application No. 16/773,583, filed on Jan. 27, 2020, now Pat. No. 11,559,613.

(60) Provisional application No. 62/851,803, filed on May 23, 2019, provisional application No. 62/802,031, filed on Feb. 6, 2019.

(51) Int. Cl.
*A61M 1/02* (2006.01)
*A61M 1/36* (2006.01)
*B01D 21/26* (2006.01)

(52) U.S. Cl.
CPC .......... *A61M 1/029* (2013.01); *A61M 1/0281* (2013.01); *A61M 1/3696* (2014.02); *B01D 21/26* (2013.01); *A61M 2202/0415* (2013.01); *A61M 2202/0427* (2013.01)

(58) Field of Classification Search
CPC .. A61M 1/029; A61M 1/3696; A61M 1/0281; B01D 21/26
See application file for complete search history.

(56) References Cited

U.S. PATENT DOCUMENTS

| | | |
|---|---|---|
| 3,693,649 A | 9/1972 | Gordon et al. |
| 5,456,885 A | 10/1995 | Coleman et al. |
| 5,577,513 A | 11/1996 | Van Vlasselaer |
| 5,707,876 A | 1/1998 | Levine |
| 6,123,655 A | 9/2000 | Fell |
| 6,465,256 B1 | 10/2002 | Iskra |
| 7,074,577 B2 | 7/2006 | Haubert et al. |

(Continued)

FOREIGN PATENT DOCUMENTS

| | | |
|---|---|---|
| CN | 105498293 | 4/2016 |
| WO | WO 2005/087292 | 9/2005 |

(Continued)

*Primary Examiner* — Benjamin L Lebron
(74) *Attorney, Agent, or Firm* — Levine Bagade Han LLP

(57) ABSTRACT

Apparatus and methods for concentrating platelet-rich plasma is described herein. One variation may generally comprise a tube having a length and defining a channel within and one or more ports located at a proximal end of the tube and in fluid communication with the channel. A plunger may slidably translatable within the channel while forming a seal against an inner surface of the channel and a float may have a pre-selected density and defining a concave interface surface, wherein the float is slidably contained within the channel such that the concave interface surface is in apposition to the one or more ports.

10 Claims, 5 Drawing Sheets

(56) References Cited

U.S. PATENT DOCUMENTS

| | | |
|---|---|---|
| 7,077,273 B2 | 7/2006 | Ellsworth et al. |
| 7,153,477 B2 | 12/2006 | DiCesare et al. |
| 7,179,391 B2 | 2/2007 | Leach et al. |
| 7,223,346 B2 | 5/2007 | Dorian et al. |
| 7,329,534 B2 | 2/2008 | Haubert et al. |
| 7,358,095 B2 | 4/2008 | Haubert et al. |
| 7,374,678 B2 | 5/2008 | Leach et al. |
| 7,445,125 B2 | 11/2008 | Ellsworth et al. |
| 7,470,371 B2 | 12/2008 | Dorian et al. |
| 7,771,590 B2 | 8/2010 | Leach et al. |
| 7,780,860 B2 | 8/2010 | Higgins et al. |
| 7,845,499 B2 | 12/2010 | Higgins et al. |
| 7,947,236 B2 | 5/2011 | Losada et al. |
| 7,992,725 B2 | 8/2011 | Leach et al. |
| 8,012,742 B2 | 9/2011 | Haubert et al. |
| 8,048,297 B2 | 11/2011 | Leach et al. |
| 8,048,321 B2 | 11/2011 | Leach et al. |
| 8,119,013 B2 | 2/2012 | Leach et al. |
| 8,177,072 B2 | 5/2012 | Chapman et al. |
| 8,187,477 B2 | 5/2012 | Dorian et al. |
| 8,236,258 B2 | 8/2012 | Leach et al. |
| 8,328,024 B2 | 12/2012 | Leach et al. |
| 8,348,066 B2 | 1/2013 | Ellsworth |
| 8,377,395 B2 | 2/2013 | Coleman |
| 8,394,342 B2 | 3/2013 | Felix et al. |
| 8,445,264 B2 | 5/2013 | Seubert et al. |
| 8,474,630 B2 | 7/2013 | Dorian et al. |
| 8,506,823 B2 | 8/2013 | Chapman et al. |
| 8,511,479 B2 | 8/2013 | Chapman et al. |
| 8,511,480 B2 | 8/2013 | Chapman et al. |
| 8,518,272 B2 | 8/2013 | Hoeppner |
| 8,596,470 B2 | 12/2013 | Leach et al. |
| 8,603,345 B2 | 12/2013 | Ross et al. |
| 8,603,346 B2 | 12/2013 | Leach et al. |
| 8,632,736 B2 | 1/2014 | Spatafore et al. |
| 8,632,740 B2 | 1/2014 | Dastane et al. |
| 8,747,781 B2 | 6/2014 | Bartfield et al. |
| 8,794,452 B2 | 8/2014 | Crawford et al. |
| 8,808,551 B2 | 8/2014 | Leach et al. |
| 8,950,586 B2 | 2/2015 | Dorian et al. |
| 8,992,862 B2 | 3/2015 | Leach et al. |
| 8,998,000 B2 | 4/2015 | Crawford et al. |
| 9,011,800 B2 | 4/2015 | Leach et al. |
| 9,079,123 B2 | 7/2015 | Crawford et al. |
| 9,114,334 B2 | 8/2015 | Leach et al. |
| 9,120,095 B2 | 9/2015 | O'Connel, Jr. |
| 9,138,664 B2 | 9/2015 | Leach et al. |
| 9,162,232 B2 | 10/2015 | Ellsworth |
| 9,239,276 B2 | 1/2016 | Landrigan et al. |
| 9,272,083 B2 | 3/2016 | Duffy et al. |
| 9,333,445 B2 | 5/2016 | Battles et al. |
| 9,339,741 B2 | 5/2016 | Newby et al. |
| 9,364,828 B2 | 6/2016 | Crawford et al. |
| 9,375,661 B2 | 6/2016 | Chapman et al. |
| 9,393,575 B2 | 7/2016 | Ellsworth et al. |
| 9,393,576 B2 | 7/2016 | Ellsworth et al. |
| 9,399,226 B2 | 7/2016 | Ellsworth et al. |
| 9,452,427 B2 | 9/2016 | Felix et al. |
| 9,642,956 B2 | 5/2017 | Landrigan et al. |
| 9,649,579 B2 | 5/2017 | Leach et al. |
| 9,656,274 B2 | 5/2017 | Ellsworth et al. |
| 9,694,359 B2 | 7/2017 | Losada et al. |
| 9,700,886 B2 | 7/2017 | Felix et al. |
| 9,714,890 B2 | 7/2017 | Newby et al. |
| 9,731,290 B2 | 8/2017 | Crawford et al. |
| 9,802,189 B2 | 10/2017 | Crawford et al. |
| 9,897,589 B2 | 2/2018 | Woodell-May |
| 9,919,307 B2 | 3/2018 | Crawford et al. |
| 9,919,308 B2 | 3/2018 | Crawford et al. |
| 9,919,309 B2 | 3/2018 | Crawford et al. |
| 9,933,344 B2 | 4/2018 | Newby et al. |
| 9,937,445 B2 | 4/2018 | King et al. |
| 10,005,081 B2 | 6/2018 | Duffy et al. |
| 10,183,042 B2 | 1/2019 | Leach et al. |
| 10,343,157 B2 | 7/2019 | Crawford et al. |
| 10,350,591 B2 | 7/2019 | Felix et al. |
| 10,376,879 B2 | 8/2019 | Crawford et al. |
| 10,393,728 B2 | 8/2019 | Woodell-May |
| 10,413,898 B2 | 9/2019 | Crawford et al. |
| 10,456,782 B2 | 10/2019 | Crawford et al. |
| 10,603,665 B2 | 3/2020 | Levine et al. |
| 10,618,044 B1 | 4/2020 | Petrie, Jr. |
| 2004/0067162 A1 | 4/2004 | Haubert et al. |
| 2013/0294983 A1 | 11/2013 | Dorian et al. |
| 2014/0135199 A1 | 5/2014 | Ellsworth et al. |
| 2015/0231626 A1 | 8/2015 | Shi et al. |
| 2017/0290993 A1 | 10/2017 | Cowan et al. |
| 2017/0304823 A1 | 10/2017 | Sparks et al. |
| 2018/0304251 A1 | 10/2018 | Ellson et al. |
| 2018/0353952 A1 | 12/2018 | Olson |
| 2020/0009304 A1 | 1/2020 | Dorian et al. |
| 2020/0009551 A1 | 1/2020 | Dorian et al. |
| 2020/0009552 A1 | 1/2020 | Crawford et al. |
| 2020/0129560 A1 | 4/2020 | Centeno et al. |
| 2020/0197929 A1 | 6/2020 | Weinstock et al. |
| 2020/0215243 A1 | 7/2020 | Dorian et al. |
| 2020/0246516 A1 | 8/2020 | Dorian et al. |
| 2020/0289720 A1 | 9/2020 | Streit |

FOREIGN PATENT DOCUMENTS

| | | |
|---|---|---|
| WO | WO 2010/115190 | 10/2010 |
| WO | WO 2018/197562 | 11/2018 |
| WO | WO 2018/197564 | 11/2018 |
| WO | WO 2018/197592 | 11/2018 |
| WO | WO 2020/013981 | 1/2020 |
| WO | WO 2020/013997 | 1/2020 |
| WO | WO 2020/154305 | 7/2020 |
| WO | WO 2020/163105 | 8/2020 |

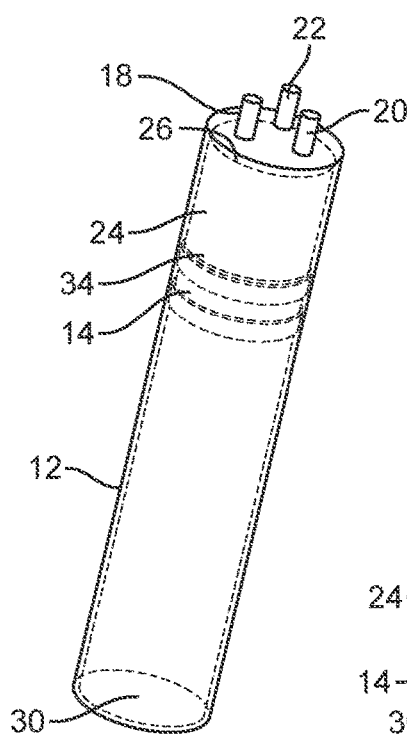 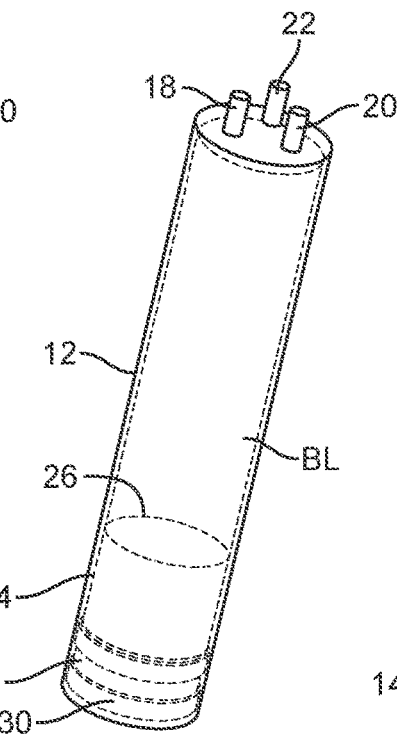 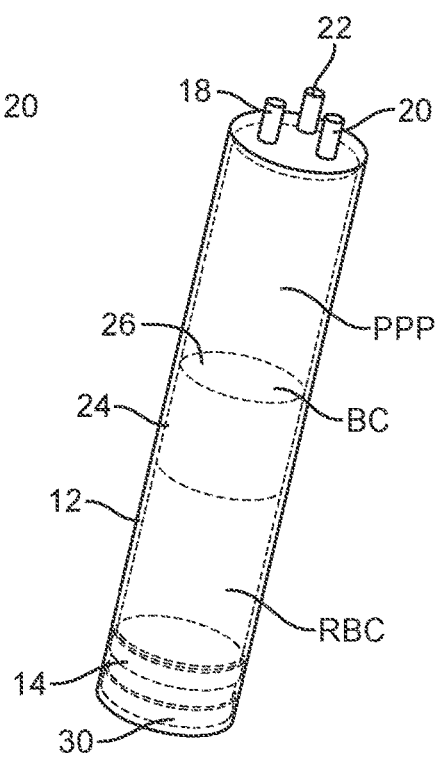
FIG. 2A    FIG. 2B    FIG. 2C
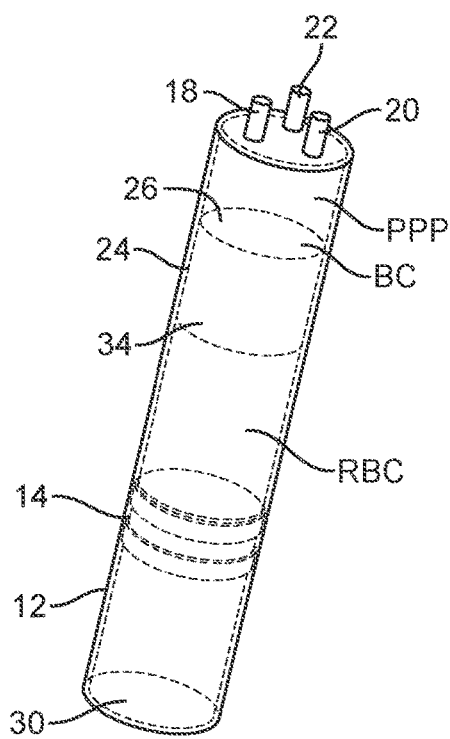 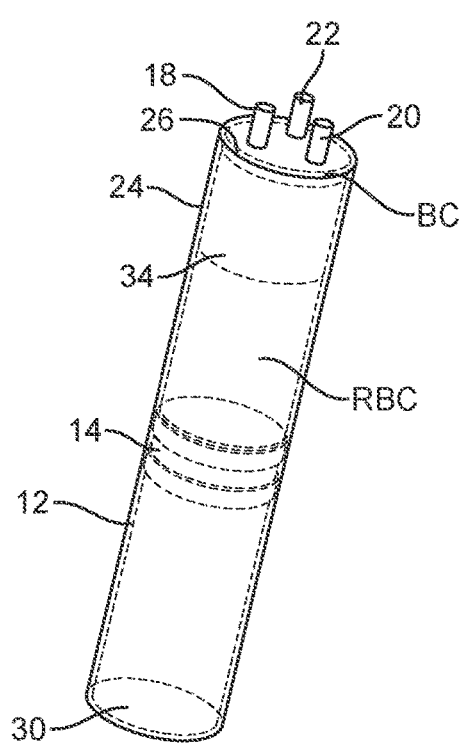
FIG. 2D    FIG. 2E

APPARATUS AND METHODS FOR CONCENTRATING PLATELET-RICH PLASMA

CROSS-REFERENCE TO RELATED APPLICATIONS

This application is a continuation of U.S. application Ser. No. 16/773,583 filed Jan. 27, 2020, which claims the benefit of priority to U.S. Prov. Apps. 62/802,031 filed Feb. 6, 2019 and 62/851,803 filed May 23, 2019, each of which is incorporated herein by reference in its entirety and for any purpose.

FIELD OF THE INVENTION

The present invention relates to apparatus and methods for separating blood components. More particularly, the present invention relates to apparatus and methods for effectively separating and removing specific components from blood.

BACKGROUND OF THE INVENTION

Blood may be fractionated and the different fractions of the blood used for different medical needs. For instance, anemia (low erythrocyte levels) may be treated with infusions of erythrocytes. Thrombocytopenia (low thrombocyte (platelet) levels) may be treated with infusions of platelet concentrate.

The sedimentation of the various blood cells and plasma is based on the different specific gravity of the cells and the viscosity of the medium. When sedimented to equilibrium, the component with the highest specific gravity (density) eventually sediments to the bottom, and the lightest rises to the top. Under the influence of gravity or centrifugal force, blood spontaneously sediments into three layers. At equilibrium the top, low-density layer is a straw-colored clear fluid called plasma. Plasma is a water solution of salts, metabolites, peptides, and many proteins ranging from small (insulin) to very large (complement components). Plasma per se has limited use in medicine but may be further fractionated to yield proteins used, for instance, to treat hemophilia (factor VIII) or as a hemostatic agent (fibrinogen). The term platelet rich plasma (PRP) is used for this component because most of the plasma proteins and platelets in the whole blood are in the plasma following slow centrifugation so the concentration of platelets in the plasma has increased while suspended in supernatant plasma. The uppermost layer after centrifugation typically contains plasma proteins only and is typically called platelet-poor plasma (PPP) due to the absence or low number of platelets as a result of a "hard spin".

The bottom, high-density layer is a deep red viscous fluid comprising a nuclear red blood cells (RBC) specialized for oxygen transport. The red color is imparted by a high concentration of chelated iron or heme that is responsible for the erythrocytes high specific gravity. Packed erythrocytes, matched for blood type, are useful for treatment of anemia caused by, e.g., bleeding. The relative volume of whole blood that consists of erythrocytes is called the hematocrit, and in normal human beings can range from about 38% to about 54%.

The intermediate layer is the smallest layer, appearing as a thin white band on top the erythrocyte layer and below the plasma, and is called the buffy coat. The buffy coat itself has two major components, nucleated leukocytes (white blood cells) and anuclear smaller bodies called platelets (or thrombocytes). Leukocytes confer immunity and contribute to debris scavenging. Platelets seal ruptures in the blood vessels to stop bleeding and deliver growth and wound healing factors to the wound site. The buffy coat may be separated from whole blood when the blood is subjected to a "hard spin" in which the whole blood is spun hard enough and long enough so that platelets sediment from plasma onto packed red cells and white cells percolate up through red cell pack to the interface between red cells and plasma.

When whole blood is centrifuged at a low speed (e.g., up to 1,000 g) for a short time (e.g., two to four minutes) white cells sediment faster than red cells and both sediment much faster than platelets. At higher speeds the same distribution is obtained in a shorter time. The method of harvesting PRP from whole blood is based on this principle. Centrifugal sedimentation that takes the fractionation only as far as separation into packed erythrocytes and PRP is called a "soft spin" which is typically used to describe centrifugation conditions under which erythrocytes are sedimented but platelets remain in suspension. "Hard spin" is typically used to describe centrifugation conditions under which erythrocytes sediment and platelets sediment in a layer immediately above the layer of erythrocytes.

The auto-transfusion equipment used to make autologous platelet concentrates requires a skilled operator and considerable time and expense and these devices require a large prime volume of blood. While many of these devices have somewhat reduced the cost and the time required, skilled operators and time are still required. Accordingly, there remains a need for simple and effective methods and devices for separating and removing components from whole blood.

SUMMARY OF THE INVENTION

The present invention relates to apparatus and methods for rapid fractionation of blood into its different components, e.g., erythrocyte, plasma, and platelet fractions. The design described herein for a buffy coat concentrator should provide platelet and white blood cell (WBC) yields comparable to other gravitational platelet separation (GPS) designs. The manufacturing costs should be lower and are easy to use. It also allows for the user to choose a desired level of buffy coat concentration. Markings on the tube can be provided to indicate the amount of platelet-depleted plasma (PPP) to be withdrawn prior to resuspension of the buffy coat to yield a desired concentration factor (the more PPP removed, the higher the float will be within the tube and hence the higher the concentration). Because platelets sediment onto a thin layer of red blood cells (RBC) trapped within the float concavity, platelet damage should be minimal and resuspension should be easier (as with GPS) than when platelets are sedimented directly onto a hard surface.

One variation may include a tube having a single port or several separate ports at a proximal end of the tube. A sterile vent may be defined at a distal end of the tube and a plunger may be slidably positioned within the tube. A tuned density float having a concavity defined in the upper float surface may be slidably positioned within the tube between the plunger and the ports. An inner surface of the tube distal to the ports and facing the interior of the tube may define a convex ceiling which mirrors the concavity of the upper float surface in a corresponding manner.

During use with one variation, the float and plunger may be positioned at a top of the tube and ready for introduction of anticoagulated blood. The float and plunger may slide down distally within the tube in unison as blood is introduced through the blood introduction port. Displaced air within the tube may escape through the sterile vent at the bottom of tube. The float may rise to an equilibrium position with the bulk of RBC packing out beneath the float and plasma PPP above the float. Hence the float may be configured to have its density tuned to automatically position itself between the two layers under centrifugation. A buffy coat overlaying a small volume of RBC may be trapped within the convex upper surface of the float.

After centrifugation, a volume of PPP may be withdrawn through the PPP port and the float and plunger may slide up the tube in unison. The volume of PPP remaining above float will determine the level of buffy coat concentration in the final buffy coat concentrate. Air may enter the space beneath the plunger via the sterile vent at the bottom of tube to replace volume of PPP removed.

A syringe may be attached to the buffy coat withdrawal port and a small volume of air may be introduced via the syringe to facilitate resuspension of the buffy coat. The tube may be inverted multiple times or shaken or swirled to resuspend the buffy coat in the remaining PPP. After resuspension, the buffy coat concentrate may be withdrawn into the syringe, ready for use.

In order to provide for a consistent, non-selectable, pre-determined concentration factor, the float or a protrusion therefrom may be configured to collide with the ceiling of the tube or to encounter some sort of mechanical stop shy of the tube ceiling in order that during product withdrawal, the float comes to rest at a position which results in a fixed volume of fluid being retained above the float.

Under this scenario, the volume above the float cannot readily be removed after PPP withdrawal unless a sterile vent is provided in the upper section of the tube to allow air to replace the volume of fluid harvested. The upper space (between the plunger and tube ceiling) can contain anticoagulant so that whole blood may be drawn directly from the patient into the device and be admixed with anticoagulant as it fills into the upper space.

The detachable plunger pull rod can optionally be used to create a vacuum within the tube by pulling and locking it in a fully extended position with the vent blocked and the blood introduction port comprised of a septum or equipped with a closed closable valve. Anticoagulant can optionally be pre-loaded into the space above the plunger in order that it be admixed with freshly drawn whole blood as it is introduced.

For certain applications, a less concentrated PRP completely devoid of RBC and WBC may be desirable. For such applications, a flat-topped float may be preferable. To produce a PRP without other contaminating cell types, the device may be spun under conditions ("soft spin") which sediment the more massive RBC and WBC beneath the buoy while platelets remain suspended above. Aside from removal of unwanted RBC and WBC, the platelet fraction would be concentrated only to the extent that the volume of RBC were removed (e.g., if the hematocrit were 50%, removing the RBC would potentially increase platelet concentration in the plasma by about two-fold over that in whole blood).

In another variation, the plunger and float may be positioned in an initial state and a vent may be capped or plugged and the upper space optionally containing anticoagulant. The blood (or anticoagulated blood) may be introduced either by pulling the plunger or collecting directly from the patient after evacuation of the tube (e.g., by pulling plunger to full extension and locking) through withdrawal port. The detachable plunger may then be detached and the withdrawal port capped.

After centrifugation, the buffy coat may form above the lowermost level of float at its equilibrium position. The PPP may be withdrawn (with vent stoppered) where the float and plunger travel in unison. The PPP withdrawal may stop when a portion of the float collides with tube ceiling. With the vent unstoppered, a syringe may be attached to the withdrawal port and a volume of air may be introduced (to facilitate resuspension). The buffy coat may be resuspended in the retained volume of PPP. The resuspended buffy coat may be withdrawn into a collection syringe, and the extracted volume replaced by air via the sterile vent.

In yet another variation, a protrusion, such as a peg, may project from the bottom of the float and a corresponding opening may be defined along a top surface of the plunger to snugly receive the protrusion into the opening. This allows for the float to couple to the plunger temporarily so that when the plunger in pulled down to introduce anticoagulated blood or anticoagulant followed by whole blood directly from the patient, the float and plunger may move down in unison. The fit of the protrusion into the plunger opening may be tight enough that they remain coupled when the plunger is pulled down. The buoyant force on the float during centrifugation is sufficient to urge the protrusion out of the opening so that the float 24 can rise and eventually find its equilibrium position in the separated blood.

One variation of a separation apparatus described herein may generally comprise a tube having a length and defining a channel within and one or more ports located at a proximal end of the tube and in fluid communication with the channel. A plunger may slidably translatable within the channel while forming a seal against an inner surface of the channel and a float may have a pre-selected density and defining a concave interface surface, wherein the float is slidably contained within the channel such that the concave interface surface is in apposition to the one or more ports.

One variation for separating components from blood may generally comprise displacing a float and a plunger from a first position within a tube to a second position by introducing a volume of blood into the tube and applying a centrifugal force to the volume of blood contained within the tube such that the blood forms at least a first fractional layer and a second fractional layer and the float positions itself between the first and second fractional layers, wherein the float has a pre-selected density and defines a concave interface surface. Once centrifuged, at least the first fractional layer may be withdrawn from the tube via at least one port defined at a proximal end of the tube such that the float and plunger are moved from the second position back towards the first position.

BRIEF DESCRIPTION OF THE DRAWINGS

FIGS. 2A to 2E show perspective views of one variation for use of the tube.

DETAILED DESCRIPTION OF THE INVENTION

Throughout the description, terms such as "top", "above, "bottom", "below" are used to provide context with respect to the relative positioning of components when, e.g., a container tube with fractional components of blood are positioned when the longitudinal axis of a container tube is positioned upright or non-horizontally. Such description is used for illustrative purposes only.

As discussed herein, when sedimented to equilibrium, the component with the highest specific gravity (density) eventually sediments to the bottom, and the lightest rises to the top. Under the influence of gravity or centrifugal force, blood spontaneously sediments into three layers. At equilibrium the top, low-density layer is a straw-colored clear fluid called plasma. The term platelet-rich plasma (PRP) is used for this component because most of the plasma proteins and platelets in the whole blood are in the plasma following slow centrifugation so the concentration of platelets in the plasma has increased while suspended in supernatant plasma. The bottom, high-density layer comprises sedimented red blood cells (RBC). The intermediate layer, if the blood is subjected to further centrifugation, is called the buffy coat.

The present invention relates to apparatus and methods for rapid fractionation of blood into its different components, e.g., erythrocyte, plasma, and platelet fractions. The design described herein for a buffy coat concentrator should provide platelet and white blood cell (WBC) yields comparable to other gravitational platelet separation (GPS) designs. The manufacturing costs should be lower and are easy to use. It also allows for the user to choose a desired level of buffy coat concentration. Markings on the tube can be provided to indicate the amount of platelet-depleted plasma (PPP) to be withdrawn prior to resuspension of the buffy coat to yield a desired concentration factor (the more PPP removed, the higher the float will be within the tube and hence the higher the concentration). Because platelets sediment onto a thin layer of red blood cells (RBC) trapped within the float concavity, platelet damage should be minimal and resuspension should be easier (as with GPS) than when platelets are sedimented directly onto a hard surface.

Figure 1:
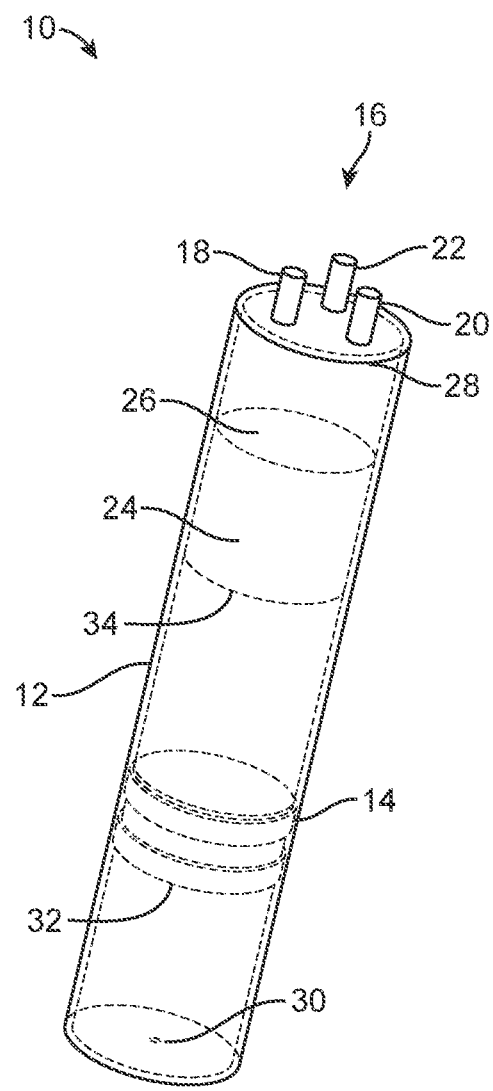
FIG. 1 shows a perspective view of one variation of a separation assembly having a float with a concavity defined on an upper surface.

The perspective view of FIG. 1 and the illustrated step-by-step description herein are sufficient to permit appreciation of the principle and method of operation. Some variants described may also be useful for certain applications/markets and can allow also for preparation of WBC-free and RBC-free platelet-rich plasma (PRP). One variation 10 is shown as having a tube 12 which may have three separate ports 16 at a proximal end of the tube 12, as shown, e.g., blood introduction port 18, PPP withdrawal port 22, and a buffy coat withdrawal port 20. A sterile vent 30 may be defined at a distal end of the tube. The plunger 14 may be slidably positioned within the tube and have a bottom circumferential seal 32 form a seal against the inner wall of the tube as well as optionally form a seal against the tube floor during centrifugation when in its lowermost position within the tube 12. This optional seal 32 may provide an extra level of assurance in preventing any blood from leaking out of the bottom of the tube under pressure developed during centrifugation.

A tuned density float 24 having a feature, for example, a flattened surface, a convex surface, or a concavity 26 defined in the upper float surface may be slidably positioned within the tube between the plunger 32 and the ports 16. The lower float surface 34 may also be configured to have various shapes, e.g., a flattened surface, a concave surface, or a convex surface. Alternatively, the lower float surface 34 may be tapered to present a sloped conical shape or a sloped surface angled from one side of the float 24 towards the opposite side of the float 24. An inner surface 28 of the tube distal to the ports and facing the interior of the tube may define a convex ceiling which mirrors the concavity 26 of the upper float surface in a corresponding manner.

While three separate ports 16 are indicated for introduction of citrated whole blood, removal of PPP and harvest of buffy coat concentrate, a single port could be sufficient. Generally, multiple use of a single port is generally frowned upon, so more than the three ports shown may also be incorporated and used, if desired.

FIGS. 2A to 2E show perspective views of one variation for use of the tube as described. FIG. 2A shows an initial condition of the tube 12 where the float 24 and plunger 14 are positioned at a top of tube and ready for introduction of anticoagulated blood. FIG. 2B shows the float 24 and plunger 14 slide down distally within the tube in unison as blood BL is introduced through the blood introduction port 18. Displaced air within the tube 12 may escape through the sterile vent 30 at the bottom of tube. FIG. 2C illustrates how under centrifugation, the float 24 rises to an equilibrium position with the bulk of RBC packing out beneath the float and plasma PPP above the float. Hence the float 24 may be configured to have its density tuned to automatically position itself between the two layers under centrifugation. For example, the float 24 may have a density which is tuned specifically for use with whole blood, e.g., 1000 to 1100 kg/m$^3$ (or specific density of 1.0 to 1.1 at 25° C.), while in other variations, the float 24 may be fabricated to have a different density, e.g., 1.03 to 1.07, etc. A buffy coat overlaying a small volume of RBC is trapped within the convex upper surface of the float.

FIG. 2D shows the tube after centrifugation where a volume of PPP is withdrawn through the PPP port 22. As the PPP is withdrawn, the float 24 and plunger 14 may slide up the tube 12 in unison. The volume of PPP remaining above float 24 will determine the level of buffy coat concentration in the final buffy coat concentrate. Air may enter the space beneath the plunger 14 via the sterile vent 30 at the bottom of tube 12 to replace volume of PPP removed.

A syringe may be attached to the buffy coat withdrawal port 20 and a small volume of air may be introduced via the syringe to facilitate resuspension of the buffy coat BC, as shown in FIG. 2E. The tube 12 may be inverted multiple times or shaken or swirled to resuspend the buffy coat BC in the remaining PPP. After resuspension, the buffy coat BC concentrate may be withdrawn into the syringe, ready for use.

In order to provide for a consistent, non-selectable, predetermined concentration factor, the float or a protrusion therefrom may be configured to collide with the ceiling of the tube or to encounter some sort of mechanical stop shy of the tube ceiling in order that during product withdrawal, the float comes to rest at a position which results in a fixed volume of fluid being retained above the float.

Under this scenario, the volume above the float 40 cannot readily be removed after PPP withdrawal unless a sterile vent 46 is provided in the upper section of the tube 12 to allow air to replace the volume of fluid harvested. The vent 46 is depicted in FIGS. 3A to 3F as a side port which can be blocked by attachment of a cap or plug 50. The figures also illustrate a detachable plunger pull rod 52 which can be used to draw blood into the device via the (center) blood introduction port 44 (in contrast to forcibly injecting blood from a syringe into the introduction port). The upper space (between the plunger 14 and tube ceiling) can contain anticoagulant so that whole blood may be drawn directly from the patient into the device and be admixed with anticoagulant as it fills into the upper space.

The depicted detachable plunger pull rod 52 can optionally be used to create a vacuum within the tube 12 by pulling and locking it in a fully extended position with the vent blocked and the blood introduction port comprised of a septum or equipped with a closed closable valve. Anticoagulant can optionally be preloaded into the space above the plunger in order that it be admixed with freshly drawn whole blood as it is introduced.

For certain applications, a less concentrated PRP completely devoid of RBC and WBC may be desirable. For such applications, a flat-topped float may be preferable. To produce a PRP without other contaminating cell types, the device may be spun under conditions ("soft spin") which sediment the more massive RBC and WBC beneath the buoy while platelets remain suspended above. Aside from removal of unwanted RBC and WBC, the platelet fraction would be concentrated only to the extent that the volume of RBC were removed (e.g., if the hematocrit were 50%, removing the RBC would potentially increase platelet concentration in the plasma by about two-fold over that in whole blood).

Figure 3A:
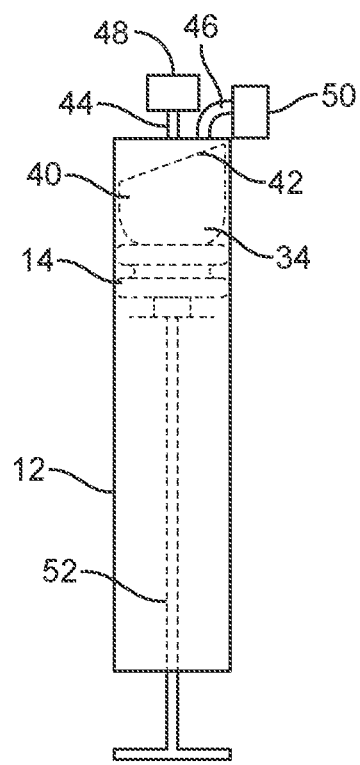
FIGS. 3A to 3F show side views of another variation for use of the tube.
Figure 3B:
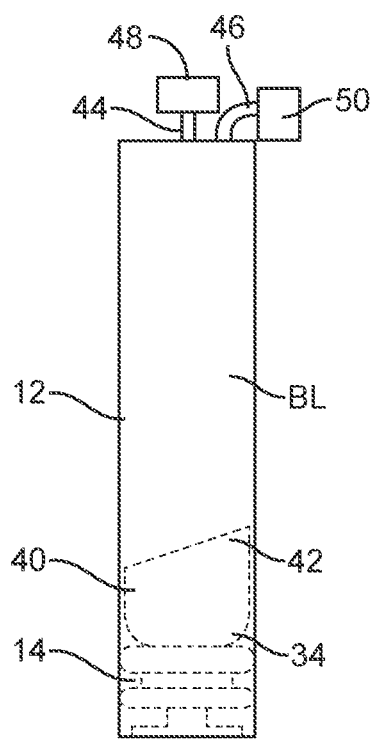

FIGS. 3A to 3F show the variation in which the plunger 14 and float 40 are positioned in an initial state, as shown in FIG. 3A. The vent 46 is shown as capped or plugged 50 and the upper space optionally containing anticoagulant. FIG. 3B illustrates how blood BL (or anticoagulated blood) may be introduced either by pulling the plunger 14 or collecting directly from the patient after evacuation of the tube (e.g., by pulling plunger to full extension and locking) through withdrawal port 44. The detachable plunger may then be detached and the withdrawal port 44 capped 48.

Figure 3C:
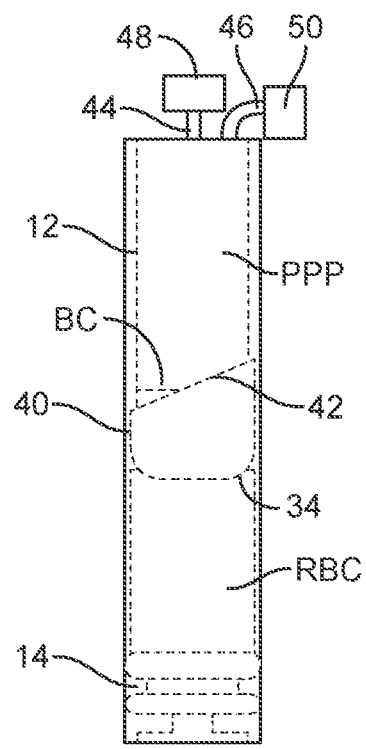
Figure 3D:
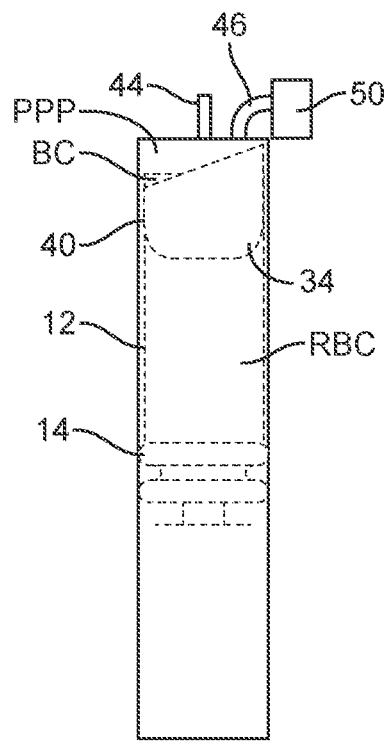
Figure 3E:
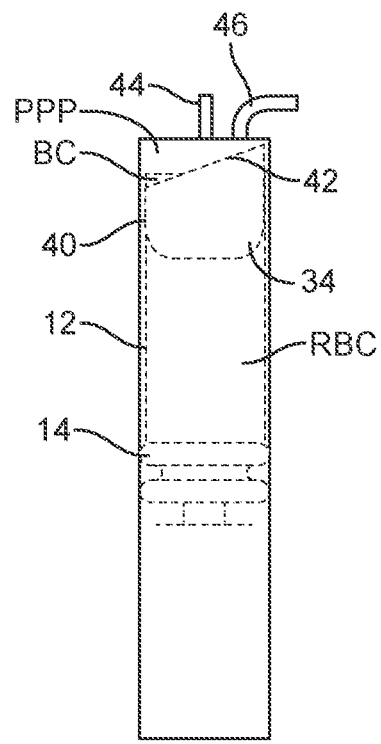
Figure 3F:
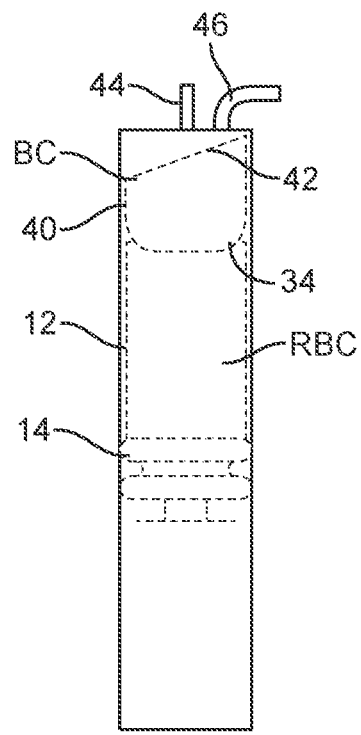

After centrifugation, as shown in FIG. 3C, the buffy coat BC may form above the lowermost level of float 40 at its equilibrium position. The PPP may be withdrawn (with vent stoppered), as shown in FIG. 3D, where the float 40 and plunger 14 travel in unison. The PPP withdrawal may stop when a portion of the interface surface 42 of the float 40 collides with tube ceiling. With the vent 46 unstoppered, as shown in FIG. 3E, a syringe may be attached to the withdrawal port 44 and a volume of air may be introduced (to facilitate resuspension). The buffy coat BC may be resuspended in the retained volume of PPP. The resuspended buffy coat BC may be withdrawn into a collection syringe, as shown in FIG. 3F, and the extracted volume replaced by air via the sterile vent.

The float 40 shown in this embodiment may be configured to be cylindrically shaped and having an angled interface surface along its upper surface which contacts the PPP and BC after centrifugation. Although shown with the present tube embodiment, the float 40 may be used with any of the variations described herein. While the upper interface surface 42 of the float 40 may define a relatively flattened surface, the interface surface 42 may instead define any number of configurations. In any of these variations where the upper float surface is concave, flattened, or convex, a layer may be applied to the upper float surface which is relatively slippery. In one variation, a silicone layer may be formed upon the upper float surface to facilitate the removal of platelets from the upper surface.

Figure 4A:
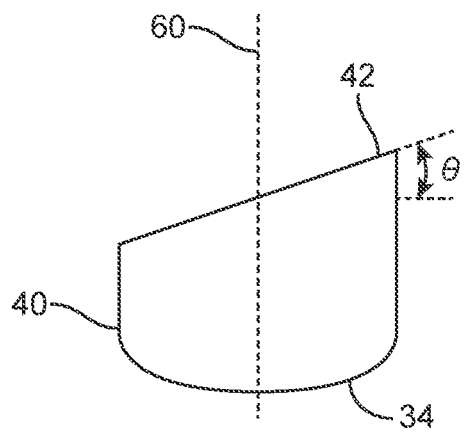
FIGS. 4A to 4D show side views of various float configurations.

As shown in the side view of FIG. 4A, the upper float interface surface 42 may be angled relative to a longitudinal axis 60 of the float 40 such that the surface preferentially slides platelets along a predefined direction. The angle Θ defining the slope of the interface surface 42 as the angle defined between a transverse plane of the float 40 and the interface surface 42 may range anywhere from 0 degrees to just under 90 degrees, but may range in some embodiments from, e.g., 2 to 60 degrees. Having the angled interface surface 42 may also allow for the blood components such as the BC to preferentially pool or collect between the tube interior wall and along the interface surface 42 allowing for ease of collection when the float is positioned near or at the upper interior surface of the tube, as shown in FIG. 3F above.

Figure 4B:
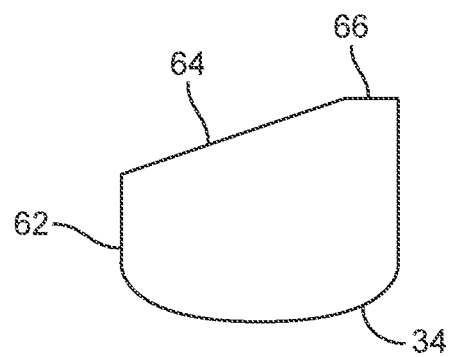
Figure 4C:
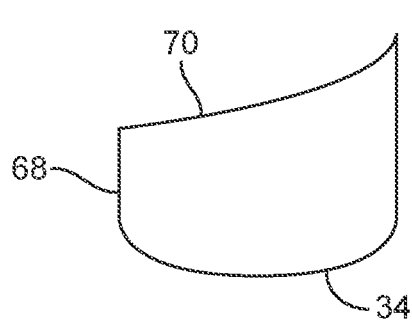
Figure 4D:
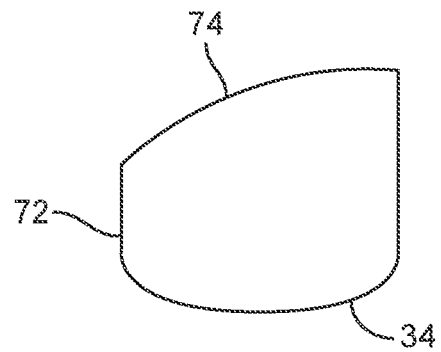

FIG. 4B shows a side view of another variation of the float 62 which may define an angled interface surface 64 which terminates at a flattened should 66. FIG. 4C shows a side view of another variation of float 68 where the interface surface 70 may be defined as a concave surface which is asymmetrically angled to slope preferentially towards one side of the float 68, as shown. FIG. 4D shows a side view of yet another variation of float 72 where the interface surface 72 may be defined as a convex surface which is also asymmetrically angled to slope preferentially towards one side of the float 72, as shown.

Figure 5:
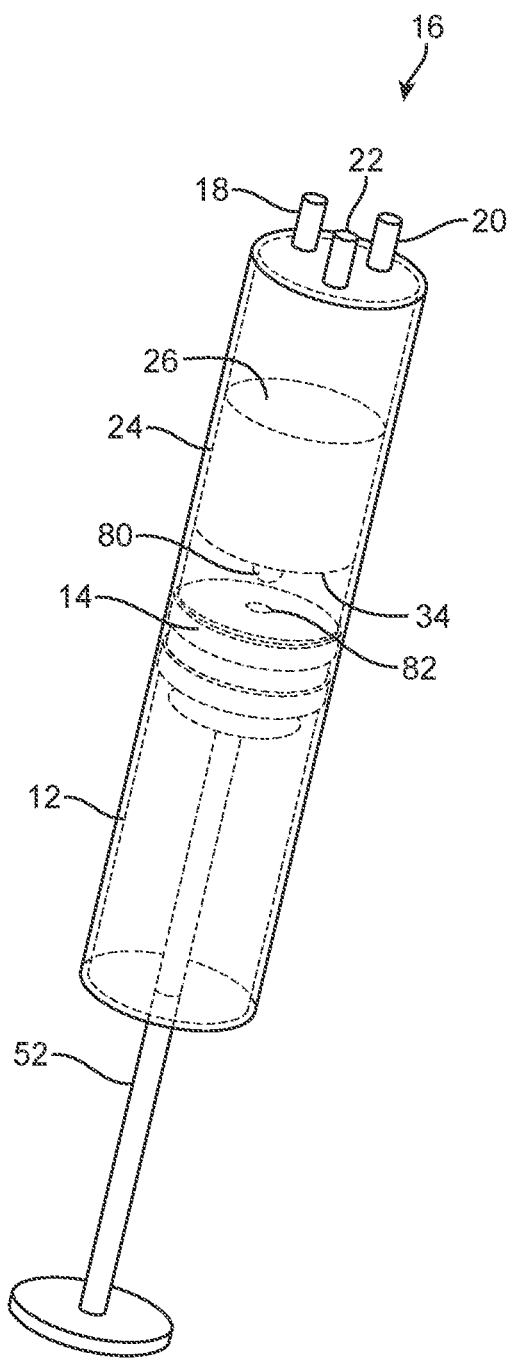
FIG. 5 shows a perspective view of yet another variation of the tube where the plunger and float may incorporate a temporary securement mechanism.

Another embodiment is illustrated in the perspective view of FIG. 5 in which a protrusion 80, such as a peg, may project from the bottom of the float 24. A corresponding opening 82 may be defined along a top surface of the plunger 14 to snugly receive the protrusion 80 into the opening 82. This allows for the float 24 to couple to the plunger 14 so that when the plunger 14 in pulled down to introduce anticoagulated blood or anticoagulant followed by whole blood directly from the patient, the float 24 and plunger 14 may move down in unison. Any of the float variations described herein may be utilized with this embodiment or any of the other embodiments as described.

If desired, anticoagulant can first be pulled into the tube 12 and then (with all ports 16, including the vent port, capped) the plunger 14 can be pulled all the way down to create a vacuum and locked in place (e.g., by a twist engaging a latch between pull rod 52 or plunger 14 and tube 12). Then a blood line stuck into the patient's vein can be attached to the tube 12 either via a septum port or Luer port with valve (so that the vacuum is maintained within the tube 12 until the blood line is connected).

Alternatively, an anticoagulant may be preloaded in the tube 12 so that the user could merely pull a vacuum using the pull rod 52 and then connect a blood line to the patient (without needing to add anticoagulant).

The fit of the protrusion 60 into the plunger opening 62 may be tight enough that they remain coupled when the plunger 52 is pulled down. The buoyant force on the float 24 during centrifugation is sufficient to urge the protrusion 60 out of the opening 62 so that the float 24 can rise and eventually find its equilibrium position in the separated blood.

The apparatus and methods disclosed above are not limited to the individual embodiments which are shown or described but may include combinations which incorporate individual features between the different variations. Modification of the above-described assemblies and methods for carrying out the invention, combinations between different variations as practicable, and variations of aspects of the invention that are obvious to those of skill in the art are intended to be within the scope of the claims.

What is claimed is:

1. A separation apparatus, comprising
   a tube having a length and defining a channel within;
   one or more ports located at a proximal end of the tube and in fluid communication with the channel; and
   a float having a pre-selected density and an interface surface defined by a first interface portion and a second interface portion extending from the first interface portion, wherein the float is slidably contained within the channel such that the interface surface is in apposition to the one or more ports, and wherein the first interface portion defines a first angle relative to a transverse plane of the float and the second interface portion defines a second angle relative to the transverse plane such that the second angle is greater than the first angle whereby the interface surface is configured to preferentially pool blood components along the second interface portion.

2. The apparatus of claim 1 wherein the first or second angle relative to the transverse plane is between 2 to 60 degrees.

3. The apparatus of claim 1 wherein the one or more ports comprise a blood introduction port, a PPP withdrawal port, or a buffy coat withdrawal port.

4. The apparatus of claim 1 further comprising a plunger slidably positioned within the tube.

5. The apparatus of claim 4 further comprising a pull rod attachable to the plunger.

6. The apparatus of claim 1 wherein the float has a density between a layer of RBC and a layer of PPP when the tube is centrifuged.

7. The apparatus of claim 1 wherein the float has a specific density between 1.0 to 1.07.

8. The apparatus of claim 1 wherein the interface surface comprises a concave interface surface which is configured to retain a buffy coat layer when the tube is centrifuged.

9. The apparatus of claim 1 wherein the float comprises a portion extending from the float for contact against an upper inner surface of the tube.

10. The apparatus of claim 1 wherein the interface surface is angled such that the blood components are preferentially pooled between the inner surface of the channel and the interface surface.

* * * * *